United States Patent [19]
Heil

[11] Patent Number: 6,007,506
[45] Date of Patent: Dec. 28, 1999

[54] METHOD OF USING A SHOE & SUPPORT DEVICE

[76] Inventor: Dean Heil, 16411 Creek South, Houston, Tex. 77068

[21] Appl. No.: 09/094,841

[22] Filed: Jun. 15, 1998

Related U.S. Application Data

[63] Continuation-in-part of application No. 08/677,518, Jul. 10, 1996.

[51] Int. Cl.$^6$ ........................................................ A61F 5/00
[52] U.S. Cl. .................................................. 602/23; 602/5
[58] Field of Search ............................... 602/23, 27–29, 602/5; 36/71.5, 140, 148, 132, 136

[56] References Cited

U.S. PATENT DOCUMENTS

| | | | |
|---|---|---|---|
| 607,243 | 7/1898 | Huff | 602/65 |
| 810,355 | 1/1906 | Semelder | 602/29 |
| 1,129,525 | 2/1915 | Severy . | |
| 1,350,944 | 8/1920 | Severy . | |
| 1,585,828 | 5/1926 | Bierig . | |
| 1,792,155 | 2/1931 | Fisher . | |
| 2,320,800 | 6/1943 | Sabel et al. . | |
| 2,382,821 | 8/1945 | Rosenthal . | |
| 2,444,839 | 7/1948 | Markula . | |
| 2,477,591 | 8/1949 | Follis . | |
| 2,516,872 | 8/1950 | Hauser et al. . | |
| 2,536,454 | 1/1951 | McIntyre . | |
| 2,567,195 | 9/1951 | Ellery . | |
| 2,712,310 | 7/1955 | Giambra . | |
| 2,949,111 | 8/1960 | Ruotoistenmaki . | |
| 3,067,531 | 12/1962 | Scott et al. . | |
| 3,268,912 | 8/1966 | Whelan | 602/65 X |
| 3,589,359 | 6/1971 | Hill | 602/27 |
| 3,805,773 | 4/1974 | Sichau | 602/27 |
| 3,834,377 | 9/1974 | Lebold | 128/80 H |
| 3,948,253 | 4/1976 | Burke | 128/80 |
| 3,986,501 | 10/1976 | Schad | 602/28 |
| 4,102,337 | 7/1978 | Golia | 602/27 |
| 4,169,467 | 10/1979 | Rabischong et al. | 605/5 |
| 4,280,489 | 7/1981 | Johnson, Jr. | 602/27 |
| 4,459,980 | 7/1984 | Perser et al. | 602/27 |
| 4,693,239 | 9/1987 | Clover, Jr. | 602/27 |
| 4,719,926 | 1/1988 | Nelson | 602/27 |
| 4,809,686 | 3/1989 | Crane | 128/80 |
| 4,844,094 | 7/1989 | Grim | 602/27 |
| 4,865,023 | 9/1989 | Craythorne et al. | 602/27 |
| 4,922,630 | 5/1990 | Robinson | 36/89 |
| 4,936,295 | 6/1990 | Crane | 128/80 |
| 4,958,447 | 9/1990 | DuPree | 36/101 |
| 4,962,760 | 10/1990 | Jones | 602/27 |
| 4,964,402 | 10/1990 | Grim et al. | 602/27 |
| 4,966,134 | 10/1990 | Brewer | 602/27 |
| 4,974,583 | 12/1990 | Greitas | 602/27 |
| 4,977,891 | 12/1990 | Grim | 602/27 |
| 5,007,416 | 4/1991 | Burns et al. | 602/27 |
| 5,088,478 | 2/1992 | Grim | 602/27 |
| 5,090,138 | 2/1992 | Borden | 601/27 X |
| 5,094,232 | 3/1992 | Harris et al. | 602/16 |
| 5,183,036 | 2/1993 | Spademan | 602/10 |
| 5,226,875 | 7/1993 | Johnson | 602/27 |
| 5,282,483 | 2/1994 | Wang | 602/22 |

(List continued on next page.)

FOREIGN PATENT DOCUMENTS

346244  12/1989  European Pat. Off. .................. 602/65

*Primary Examiner*—Richard J. Apley
*Assistant Examiner*—Denise Pothier
*Attorney, Agent, or Firm*—Guy McClung

[57] ABSTRACT

A foot support device for use with a shoe has been invented, the foot support device, in one aspectc having two spaced-apart side posts, each having a bottom end connectible to a side of the shoe and a top end, a front member having a top end and a bottom end connectible to a top part of the shoe and spaced-apart from each of the side posts, and a cuff connected to the top end of the two sdie posts and to the top of the front member. In one aspect such a device has one or more upwardly projecting members that are releasably connectible to a knee brace to maintain the brace in a desired position with respect to a wearer's knee. Methods are also provided for using such devices.

9 Claims, 11 Drawing Sheets

U.S. PATENT DOCUMENTS

| | | | |
|---|---|---|---|
| 5,366,439 | 11/1994 | Peters | 602/27 |
| 5,421,822 | 6/1995 | Wang | 602/27 |
| 5,429,588 | 7/1995 | Young et al. | 602/27 |
| 5,445,603 | 8/1995 | Wilkerson | 602/27 |
| 5,449,005 | 9/1995 | Echols | 602/27 |
| 5,464,385 | 11/1995 | Grim | 602/27 |
| 5,490,831 | 2/1996 | Myers et al. | 602/26 |
| 5,497,566 | 3/1996 | Kousaka et al. | 36/81 |
| 5,507,720 | 4/1996 | Lampropoulos | 602/27 |
| 5,509,217 | 4/1996 | Condini | 36/10 |
| 5,718,673 | 2/1998 | Shipstead | 602/27 |
| 5,769,290 | 6/1998 | Pestana | 224/178 |
| 5,769,803 | 6/1998 | Brossard | 602/19 |

METHOD OF USING A SHOE & SUPPORT DEVICE

RELATED APPLICATION

This is a continuation-in-part of U.S. application Ser. No. 08/677,518 filed Jul. 10, 1996 entitled "Foot Support" which is incorporated fully herein for all purposes.

BACKGROUND OF THE INVENTION

1. Field of the Invention

This invention is directed to a foot support, an ankle support, and, in one particular aspect, to a support that supports a drop foot and inhibits both undesirable foot inversion and eversion.

2. Description of Related Art

The prior art discloses a wide variety of ankle braces, orthopedic shoes, and drop foot supports. Typically these devices attempt to address problems associated with drop foot, unwanted foot inversion or introversion (movement of the foot—or inward falling of ankle)—inwardly, or unwanted foot eversion (movement jig of the foot—or ankle—outwardly. Many of the prior art devices are complex, cumbersome, difficult to make and install, and uncomfortable to the wearer.

There has long been a need for a foot support that satisfactorily deals with the three problems stated above. There has long been a need for such a support that is easily made and easily installed. There has long been a need for such a support that is useful with a variety of commercially available footwear without requiring any change in the footwear. There has long been a need for such a support which is not unduly uncomfortable for the wearer. There has long been a need for such a support that can flex and have a range of motion to accommodate movement of the wearer's leg, ankle, and foot.

SUMMARY OF THE PRESENT INVENTION

The present invention, in one embodiment, discloses a device for support for a foot. The device is used with a shoe. In certain aspects the device includes one post, or two spaced-apart posts one on either side at the heel of the shoe, the post or posts releasably or permanently connected to the shoe. Fasteners can be used for this which extend through the sides of the shoe. The posts may have an upper outwardly curved portion to accommodate outwardly protruding ankle-bone parts of a user. A front member is permanently or releasably connected to a front part of the shoe (e.g. but not limited to a tongue of the shoe). Suitable fasteners and/or VELCRO (TM) material or other releasably-cooperating hook-tie material may be used. In one aspect a shoe is used which is originally manufactured with cloth on its tongue that releasably cooperates with the material on the front member. Many commercially available shoes are made with such material. An upper cuff wraps around a user's ankle and encompasses upper portions of the posts and of the front member. Suitable fasteners and/or VELCRO (TM) material or other releasably-cooperating hook-tie material may be used to releasably connect the posts and/or front member to the cuff. The cuff may be made of any suitable soft and/or spongy material. A VELCRO (TM) material strap may be used around the cuff and, in one aspect, the strap is secured to the cuff. The strap may have VELCRO (TM) material on both sides and the cuff may have such material on its outer surface.

The present invention, in one embodiment, discloses a foot support system that has a belt or strip that is releasably secured around a person's lower leg and one or more support posts that are releasably held by the strap. The support post(s) extends from the strap down into a boot, sandal, or shoe worn on the person's foot. A lower portion of the support post is releasably connected to an interior part of the rear upper of the shoe. In another aspect two such support posts are used, one on each side of the ankle.

In one embodiment the strap has a first strap portion that is releasably securable around a person's lower leg, (e.g. with a safety pin, or clip, a two-part snap, a buckle arrangement, releasably cooperating fastener material ("RCFM") such as VELCRO (TM) material on different parts of the first strap portion), and a second strap portion connected to the first strap portion and able to be placed over an upper part of a support post to releasably hold it while permitting some flexing and limited restricted movement of the upper part of the support post with respect to the strap depending on the flexibility of the strap, flexibility of the support post, and tightness with which the second strap portion is held to the first strap portion (e.g. with a safety pin, a two-part snap, a clip, or releasably cooperating fastener material). Velcro™ material may be used on the upper part of the support post and on the strap to releasably hold the upper part of the support post to the strap.

In certain embodiments the lower part of the support post(s) rests on, (but is not connected or secured to, an inner or outer sole of the shoe or to a heel), but is easily releasably secured to an inside shoe side wall surface near the rear end of the shoe. In another embodiment the support post (or posts) does rest on the sole. In certain aspects "male" releasably cooperating fastener material on the lower part of a support post sufficiently mates with the fabric already present in a wide variety of commercially available shoes that no corresponding fastener material needs to be added to the shoes as purchased. Alternatively a small piece of such "female" fastener material may be sewn or glued on an interior shoe surface for contact by the "male" fastener material on the lower part of the support post. In another embodiment a relatively flat receptacle made, e.g. of cloth or thin plastic, is affixed to the inside of the shoe for receiving and holding a lower end of the support post. This receptacle may be secured to the inside or outside of the shoe. In other embodiments the lower end of the support post is belted to the outside of the shoe, received and held in a recess in the heel or a recess between the heel and sole, or a U-shaped support is used whose lower flat portion either passes through a hole or is releasably held in a recess in the sole or heel with the two uppersides of the U serving as support posts.

In certain embodiments, the present invention discloses: a system for supporting a foot, the foot joined to the leg by an ankle joint, the leg having a lower leg portion above the ankle joint, the system having releasable securement means for selective securement around the lower leg portion, at least one support post with an upper part releasably holdable by the releasable securement means, the at least one support post having a lower part, and the lower part of the at least one support post connected to a rear portion of footwear to be worn on the foot; such a system wherein the lower part of the at least one support post is releasably connected to the rear portion of the footwear; such a system wherein the lower part of the at least one support post and the rear portion of the footwear each have an amount of releasably cooperating fastener material to releasably connect the lower part to the footwear; such a system wherein the amount of releasably cooperating footwear material of the footwear is within the footwear; such a system wherein the lower part of the at least one support post has a base and the base extends from adjacent a portion of a heel of the foot to a point adjacent a portion of the foot forward of the ankle joint; such a system wherein the at least one support post is a first support post and a second support post, the first support post disposable on a first side of the ankle joint and the second support post disposable on a second side of the ankle joint opposite the first side of the ankle joint; such a system wherein the releasable securement means is an expandable elastic cuff; such a system wherein the releasable securement means is a first strap having a first end and a second end, the ends securable to each other with releasably cooperating fastener material on each end; such a system further having a secondary strap connected to the first strap, the secondary strap releasable securable to the first strap to hold the upper part of the at least one support post against the leg; such a system wherein the at least one support post is flexible yet rigid enough to provide support of the foot; such a system including the footwear whose rear portion has the lower part of the at least one support post connected thereto; such a system wherein an inner part of the rear portion of the footwear has cloth thereon and the lower part of the at least one support post has releasable cooperating fastener material that releasably cooperates with the cloth to releasably hold the lower part to the cloth; such a system wherein the upper part of the at least one support post has releasable cooperating fastener material thereon and the releasable securement means has corresponding releasable cooperating fastener material so that the upper part is releasably holdable by the releasable securement means; such a system wherein the at least one support post has a mid portion which projects outwardly so that the mid portion does not contact a wearer of the system; such a system wherein the footwear has a slot therethrough through the rear portion thereof and the at least one support post has a hasp member insertable through the slot and the at least one support post has a flexible tongue releasably insertable through the hasp member to releasably hold the at least one support post to the footwear; such a system having a receptacle connected to the footwear having a receptacle recess, the receptacle recess sized and configured to releasably receive and hold the lower part of the at least one support post; such a system for supporting a foot, the foot joined to the leg by an ankle joint, the leg having a lower leg portion above the ankle joint, the system having releasable securement means for selective securement around the lower leg portion, two support posts each with an upper part each releasably holdable by the releasable securement means, and with a lower part, the lower part of the support posts releasably connected to a rear portion of footwear to be worn on the foot, the lower part of each support post having a base extending from adjacent a portion of a heel of the foot to a point adjacent a portion of the foot forward of the ankle joint, the two support posts comprising a first support post and a second support post, the first support post disposable on a first side of the ankle joint and the second support post disposable on a second side of the ankle joint opposite the first side of the ankle joint. The present invention discloses a support post for use with a system for supporting a foot, the foot joined to the leg by an ankle joint, the leg having a lower leg portion above the ankle joint, releasable securement means for selective securement around the lower leg portion, and footwear to be worn on the foot, the support post comprising an upper part releasably holdable by the releasable securement means, and a lower part, connectable to a rear portion of footwear to be worn on the foot.

As discussed and shown in detail below, any of the support posts or members described or claimed herein may be either permanently or releasably attached or connected to the inside or outside of footwear. Also, a support post according to this invention may extend all the way down to touch the inner sole or inner floor of footwear or it may extend to such a point that it terminates above the sole or floor. A support post may be attached or connected to footwear with any known fastener or adhesive (e.g. glue) or it may be sewn to footwear. In certain embodiments rigid plastic is used for the support post(s). In certain embodiments a hole through the support post adjacent the projecting portion of a person's ankle bone receives and accommodates the bone so that it does not rub against the support post. In certain embodiments of systems according to this invention there is no member, plate, or strip connected to the support post(s) and extending beneath a wearer's foot or heel (other than footwear itself).

The present invention discloses, in certain embodiments, a system for supporting a foot, the foot joined to the leg by an ankle joint, the leg having a lower leg portion above the ankle joint, the system having releasable securement apparatus for selective securement around the lower leg portion, at least one support post with an upper part releasably holdable by the releasable securement apparatus, the at least one support post having a lower part, and the lower part of the at least one support post connected to a rear portion of footwear to be worn on the foot; such a system wherein the lower part of the at least one support post is releasably connected to the rear portion of the footwear; such a system wherein the lower part of the at least one support post and the rear portion of the footwear each have an amount of releasably cooperating fastener material to releasably connect the lower part to the footwear; such a system wherein the amount of releasably cooperating fastener material of the footwear is within the footwear; such a system wherein the lower part of the at least one support post has a base and the base extends from adjacent a portion of a heel of the foot to a point adjacent a portion of the foot forward of the ankle joint; such a system wherein the at least one support post is a first support post and a second support post, the first support post disposable on a first side of the ankle joint and the second support post disposable on a second side of the ankle joint opposite the first side of the ankle joint; such a system wherein the releasable securement apparatus is an expandable elastic cuff; such a system wherein the releasable securement apparatus is a first strap having a first end and a second end, the ends securable to each other with releasably cooperating fastener material on each end; such a system having a secondary strap connected to the first strap, the secondary strap releasably securable to the first strap to hold the upper part of the at least one support post against the leg; such a system wherein the at least one support post is flexible yet rigid enough to provide support of the foot; such a system wherein the footwear whose rear portion has the lower part of the at least one support post connected thereto is part of the system; such a system wherein an inner part of the rear portion of the footwear has cloth thereon and the lower part of the at least one support post has releasable cooperating fastener material that releasably cooperates with the cloth to releasably hold the lower part to the cloth; such a system 1 wherein the upper part of the at least one support post has releasable cooperating fastener material thereon and the releasable securement apparatus has corresponding releasable cooperating fastener material so that the upper part is releasably holdable by the releasable securement apparatus; such a system wherein the at least one support post has a mid portion which projects outwardly so that the mid portion does not contact a wearer of the system; such a system wherein the footwear has a slot therethrough through the rear portion thereof and the at least one support post has a hasp member insertable through the slot and the at least one support post has a flexible tongue releasably insertable through the hasp member to releasably hold the at least one support post to the footwear; such a system having a hole in the at least one support post for receiving and accommodating a portion of a bone of the ankle joint; such a system having a receptacle connected to the footwear having a receptacle recess, the receptacle recess sized and configured to releasably receive and hold the lower part of the at least one support post; and such a system wherein the at least one support post has a lower slot on the lower part thereof and the receptacle has a projecting member received in the lower slot for supporting the lower part of the at least one support post.

It is, therefore, an object of at least certain preferred embodiments of the present invention to provide:

New, useful, unique, efficient, nonobvious devices for foot support, and shoes and/or knee braces with such devices;

Such a support that counteracts the effects of drop foot, ankle inversion, and/or ankle eversion;

Such a support which is flexible and is releasably connected to a person's leg and shoe so that it accommodates movement of the wearer while still providing needed support;

Such a support which is not unduly uncomfortable to the wearer;

Such a support which is easily applied and easily removed;

Such a support which (although it may be) does not require attachment to a shoe, e.g. to a sole or heel; and Such a support which is useful with certain commercially available footwear without changing the footwear or adding any additional structure or device thereto.

Certain embodiments of this invention are not limited to any particular individual feature disclosed here, but include combinations of them distinguished from the prior art in their structures and functions. Features of the invention have been broadly described so that the detailed descriptions that follow may be better understood, and in order that the contributions of this invention to the arts may be better appreciated. There are, of course, additional aspects of the invention described below and which may be included in the subject matter of the claims to this invention. Those skilled in the art who have the benefit of this invention, its teachings, and suggestions will appreciate that the conceptions of this disclosure may be used as a creative basis for designing other structures, methods and systems for carrying out and practicing the present invention. The claims of this invention are to be read to include any legally equivalent devices or methods which do not depart from the spirit and scope of the present invention.

The present invention recognizes and addresses the previously mentioned problems and long-felt needs and provides a solution to those problems and a satisfactory meeting of those needs in its various possible embodiments and equivalents thereof. To one of skill in this art who has the benefits of this invention's realizations, teachings, disclosures, and suggestions, other purposes and advantages will be appreciated from the following description of preferred embodiments, given for the purpose of disclosure, when taken in conjunction with the accompanying drawings. The detail in these descriptions is not intended to thwart this patent's object to claim this invention no matter how others may later disguise it by variations in form or additions of further improvements.

DESCRIPTION OF THE DRAWINGS

A more particular description of embodiments of the invention briefly summarized above may be had by references to the embodiments which are shown in the drawings which form a part of this specification. These drawings illustrate certain preferred embodiments and are not to be used to improperly limit the scope of the invention which may have other equally effective or legally equivalent embodiments.

Photographs 17A–17H show various shoe and support device designs according to the present invention.

Photographs 18A and 18B show shoe and support device designs according to the present invention with a wearer's ankle and foot.

DESCRIPTION OF EMBODIMENTS PREFERRED AT THE TIME OF FILING FOR THIS PATENT

Figure 1A:
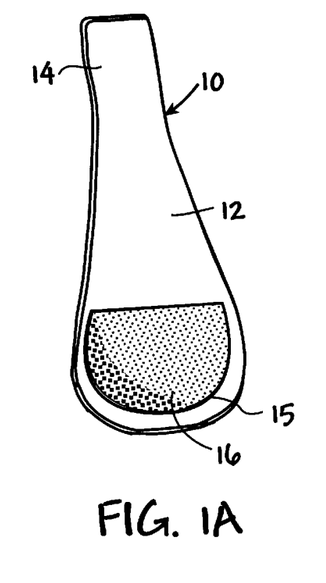
FIG. 1A is a front view of a support post according to the present invention.
Figure 1B:
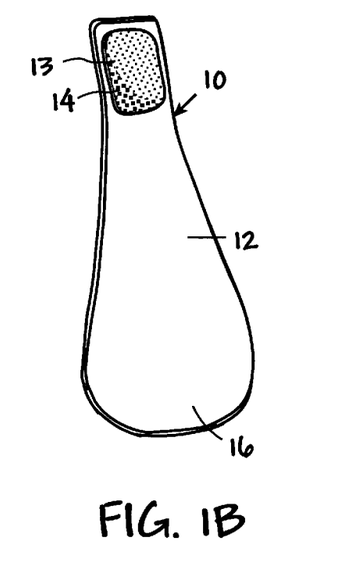
FIG. 1B is a rear view of the support post of FIG. 1A.
Figure 1C:
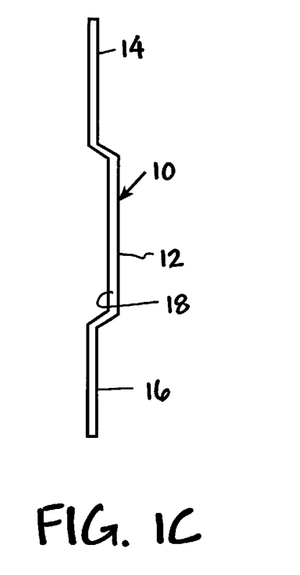
FIG. 1C is a side view of the support post of FIG. 1A.

FIG. 1A–1C show a support post 10 according to the present invention with a central body 12, an upper portion 14, and a lower portion 16. An outwardly projecting portion 18 of the central body 12 is sized and positioned so that when the support post 10 is in use the outwardly projecting portion 18 either has only minimal incidental contact with an ankle joint of a wearer or does not contact the joint at all.

To facilitate releasable connection of the ends of the support post 10, the upper portion 14 has RCFM material 13 attached thereto on a rear side for interconnection with such material on a strap worn around a wearer's leg; and the lower portion 16 has such material 15 on the front side thereof for engaging fabric on a shoe's interior or for engaging releasable cooperating fastener material on the shoe's interior. In certain embodiments "male" VELCRO (TM) material is used on the post.

It is within the scope of this invention for a support post to have a uniform thickness along its entire length. In the support post 10, which is made of LEXAN (TM) material or of a suitable plastic such or polypropylene, the upper portion 14 has a thickness of about 0.080", the central body has a thickness of about 0.080", and the lower portion has a thickness of about 0.030". Thus, the central body portion is thick enough for the necessary support and strength, yet thin enough to flex in response to torsion induced on the post by foot and leg movement and the lower portion is thin enough to prevent discomfort to the wearer while providing sufficient stiffness and strength. Such flexing makes a system with the post more comfortable for the wearer. The lower portion may be wider than the upper portion. It is within the scope of this invention for a support post to have a uniform width from top to bottom or to have a width that varies from decreasing width to increasing width or vice-versa.

Figures 2, 5:
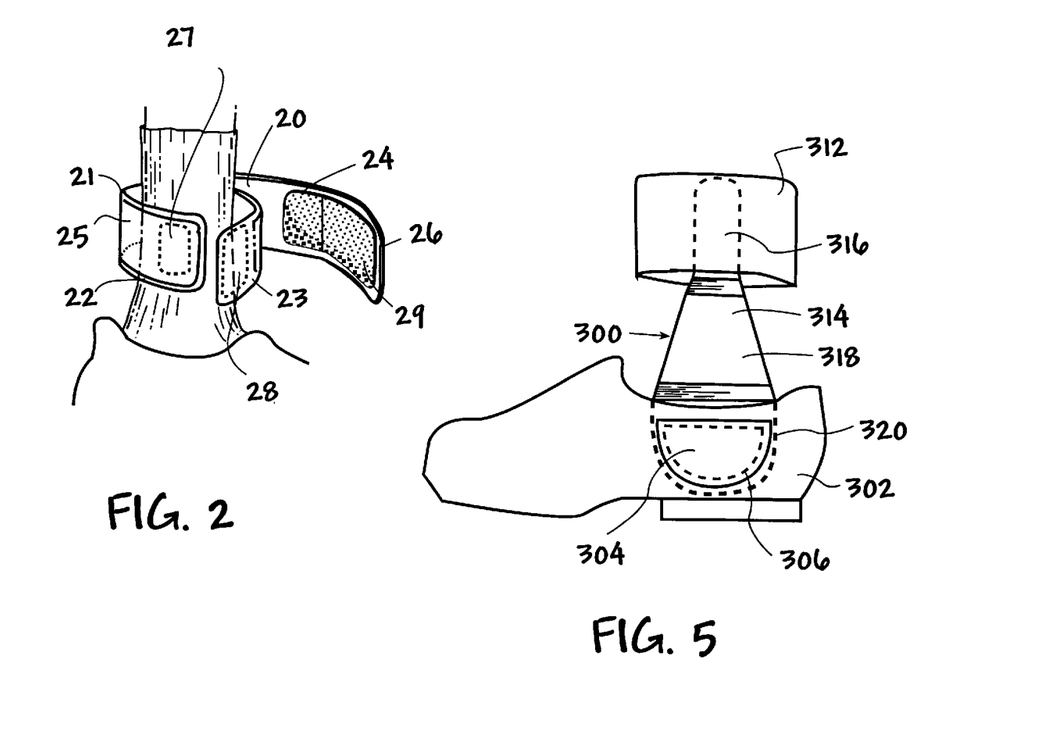
FIG. 2 is a perspective view of a strap according to the present invention.
FIG. 5 is a perspective view of a shoe according to the present invention with a foot support system according to the present invention.

FIG. 2 shows a strap 20 according to the present invention with a body 21, a first end 22, a second end 23, and a secondary strap 24 with a first end 25 and a second end 26. RCFM 27 at the first end 22 mates with RCFM 28 at the second end 23 to releasably secure the strap 20 around the lower portion of a wearer's leg and to provide an attachment point for RCFM on a support post or posts. RCFM 29 on the second end 26 of the secondary strap 24 mates with the RCFM 27 on the body 21 so the secondary strap 24 wraps over and releasably holds a support post. A secondary strap 24 of sufficient length can wrap around two support posts, one on each side of an ankle.

Figure 3:
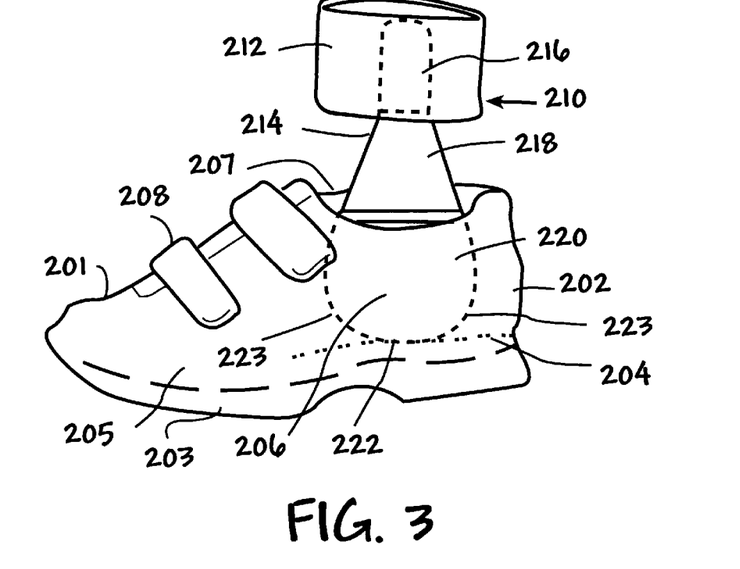
FIG. 3 is a perspective view of a shoe according to the present invention with a foot support system according to the present invention.

FIG. 3 shows a shoe 200 according to the present invention with a support system 210 according to the present invention. The shoe 200 has a heel 202, a sole 203 with a top sole surface 204, shoe upper 205 with sides 206 and 207, and closure apparatus 208. The support system 210 has an upper strap or band 212 which may be made of elastic (or any other strap disclosed herein may be used) and a support post 214. The support post 214 has a top portion 216, a mid-portion 218, and a lower portion 220 with a lower edge 222. The top portion 216 is shown as secured to the band 212, but it may be releasably secured thereto as described herein. The lower edge 222 of the lower portion 220 rests on the top sole surface 204. The post 214 is shown as secured to the interior of the shoe 200, but it may be releasably secured thereto as described herein and as shown in FIG. 4. Edges 223 are rounded to accommodate movement of the wearer. The lower portion 220 is wide enough so that part or parts of it are beyond the ankle joint of a wearer (as viewed from the side, e.g. as in FIG. 3).

Figure 4:
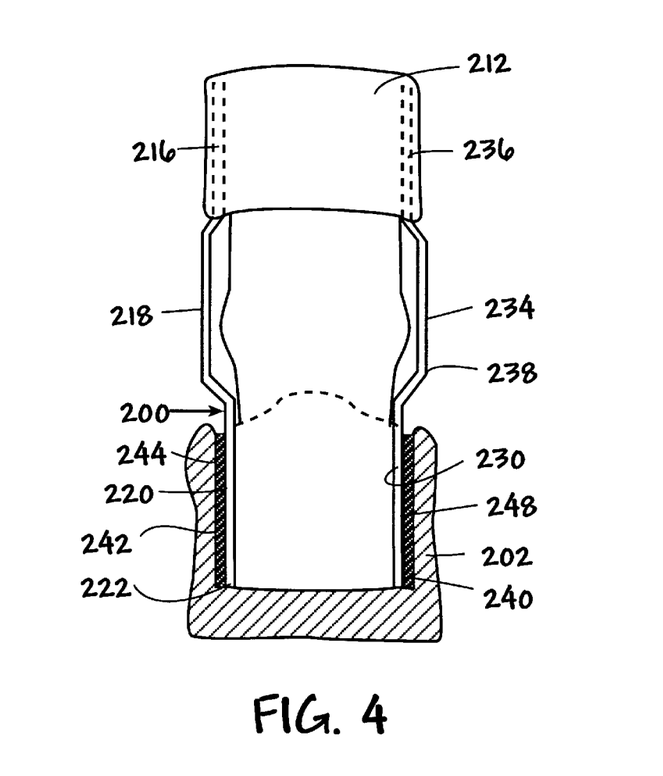
FIG. 4 is an end view partially in cross-section of the shoe of FIG. 3 with an additional support post.

As shown in FIG. 4, the support post 214 has male RCFM material 242 which mates with female RCFM material 244 on the shoe's interior. Another support post 234 has a top portion 236 and male RCFM material 240 on a lower portion 230 that mates with female RCFM material 248 on the shoe's interior. As shown mid-post portions 218 and 238 are configured so they do not touch the portion of the wearer's body adjacent and over his or her ankle-joint A on either side when the shoe is stationary and preferably so that there is little or no such contact when the wearer is walking or running.

FIG. 5 shows a shoe 300 according to the present invention with a support system 310 (like the system 210) having an upper band 312 and an upper post 314. The support post 314 has an upper portion 316, a mid-portion 318, and a lower portion 320. The lower portion 320 is sewn to a side 302 of the shoe 300 with a patch 304 and stitching 306.

Figure 10A:
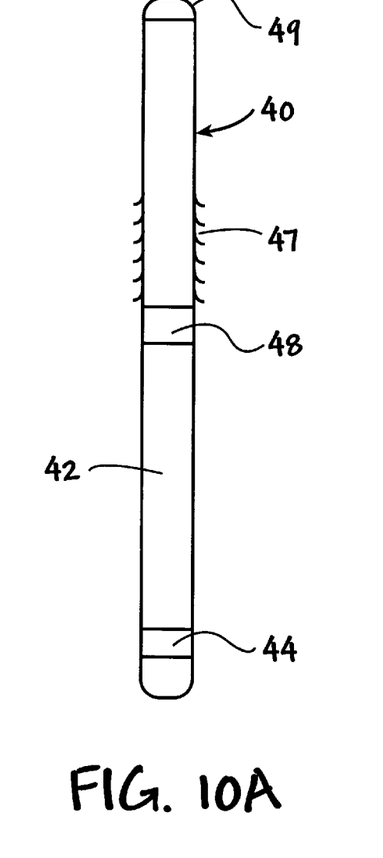
FIG. 10A is a front view of a support post according to the present invention.
Figure 10B:
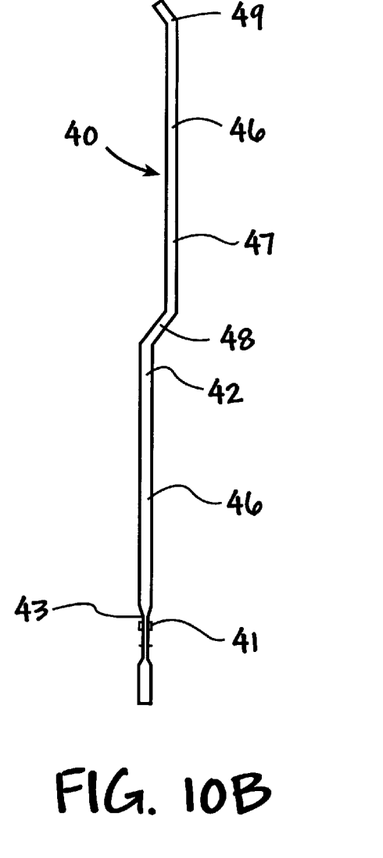
FIG. 10B is a side view of the support post of FIG. 10A.

FIGS. 10A and 10B show a support post 40 with a body 42, a ridge or button 41, an lower portion 44, a upper portion 46, a dogleg 48, a slot or recess 43, and a portion 44. A plurality of points or barbs 47 project downwardly from the body 42 for engaging material, e.g. RCFM material. Due to the dogleg 48 the lower portion 46 is disposed further outwardly from a wearer's leg than is the upper portion 46 to accommodate a projecting bone of a wearer. Preferably the lower portion 46 is positioned so that it is adjacent a wearer's ankle joint so that wear against and rubbing of the ankle joint against the post is inhibited or eliminated. The lower portion 44 may be sized for receipt in a recess of a receptacle or pocket on a shoe's interior.

Figure 11A:
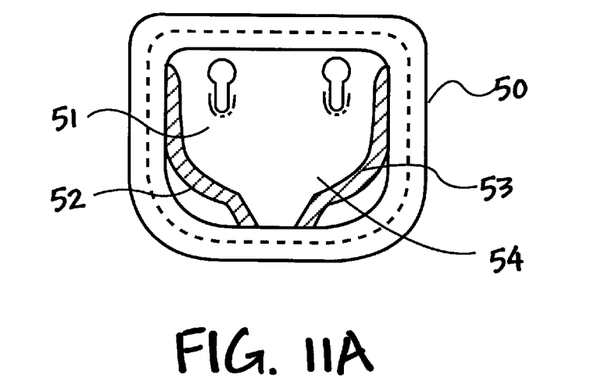
FIG. 11A is a side view in cross-section of a post receptacle according to the present invention.
Figure 11B:
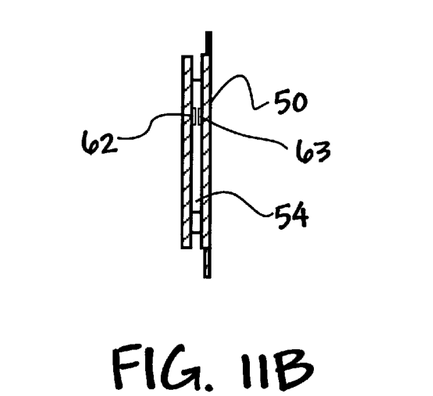
FIG. 11B is a side view of the receptacle.

FIGS. 11A and 11B show a receptacle 50 according to the present invention which may be sewn into, glued into, or releasably attached with RCFM to a shoe's interior (or exterior) for receiving and releasably holding a lower portion of a support post according to the present. In another aspect a support post is permanently or semi-permanently connected to, secured to or adhesively held to the receptacle in FIG. 11A the receptacle 50 has a body part 51 and interior ridges 52 and 53 between which is formed a recess 54 which is sized and configured to receive a lower end of a support post and in which said lower end may rotate so that the post is movable to the front and to the rear as the leg of a wearer moves. FIG. 11B shows the receptacle 50 with interior buttons or ridges 62 and 63. The slot or recess 43 (see FIG. 10B) moves on the ridges or buttons 62, 63.

Figure 12:
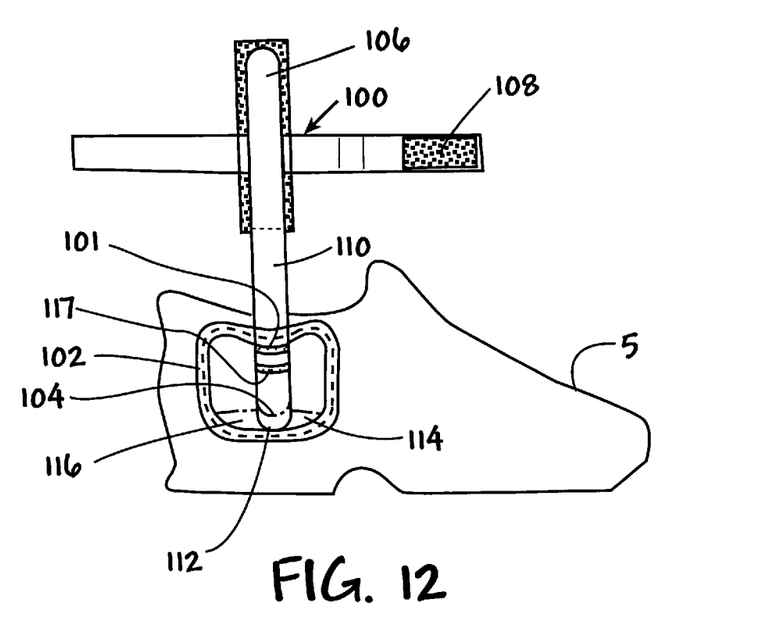
FIG. 12 is a side view of an article of footwear according to the present invention.

FIG. 12 shows a shoe S and support system 100 according to the present invention. A receptacle 102 (like the receptacle 50) is secured to an interior of the shoe S and holds a lower end 104 of a support post 110. An upper end 106 extends upwardly so that a strap 108 may be releasably wrapped around a wearer's leg. The lower end 104 may rock back and forth in a recess 112 formed between member 114 and 116 of the receptacle 102. A slot 101 (like the slot 43, FIG. 10B) moves on and along a projecting member (not shown, like the ridges or buttons 62, 63) for added stability. Another receptacle may be used on the other side of the shoe with another post. It is to be understood that "shoe" includes boots, sneakers, and comparable footwear. If it is desired that the support post be raised with respect to the shoes, a slot 117 is used on the projecting member.

Figure 6:
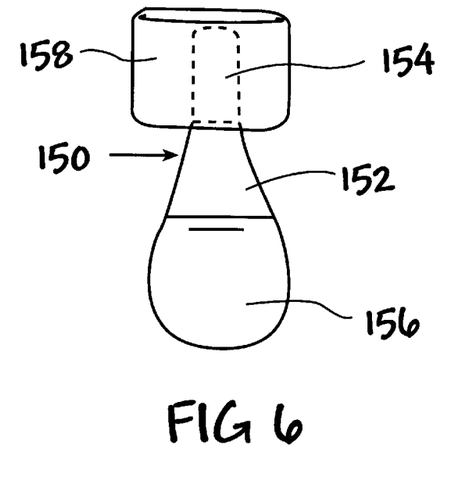
FIG. 6 is a front view of a support post according to the present invention.

FIG. 6 shows a support post 150 according to the present invention (like the post 10) with a body 152, an upper portion 154, a lower portion 156 and a leg strap 158 secured thereto or formed integrally thereof the strap 158 may be a belt with buckle (not shown); RCFM may be used to hold it around a wearer's leg; or any other suitable fastener may be employed.

Figure 7:
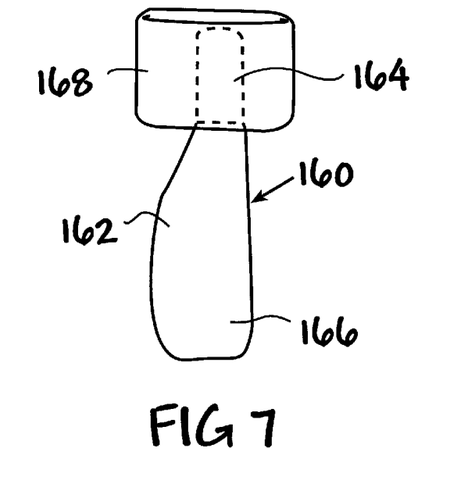
FIG. 7 is a front view of a support post according to the present invention.

FIG. 7 shows a support post 160 according to the present invention (like the post 10) with a body 162, an upper portion 164, a lower portion 166 and a leg strap 168 secured thereto or formed integrally thereof the strap 168 may be a belt with buckle (not shown); RCFM may be used to hold it around a wearer's leg; or any other suitable fastener may be employed.

Figure 8:
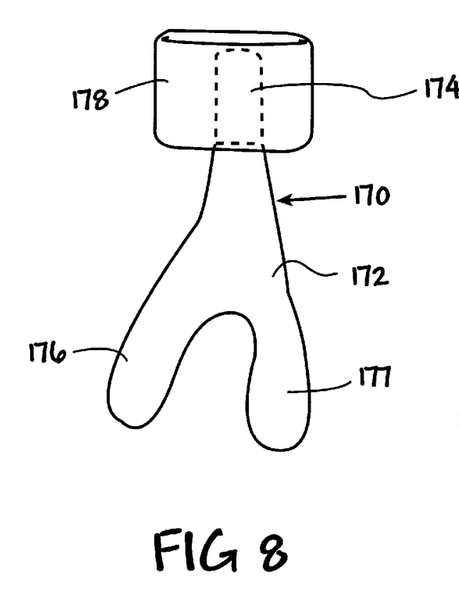
FIG. 8 is a front view of a support post according to the present invention.

FIG. 8 shows a support post 170 according to the present invention (like the post 10) with a body 172, an upper portion 174, lower portion 176 and 177, and a leg strap 178 secured thereto or formed integrally thereof the strap 178 may be a belt with buckle (not shown); RCFM may be used to hold it around a wearer's leg; or any other suitable fastener may be employed.

Figure 9:
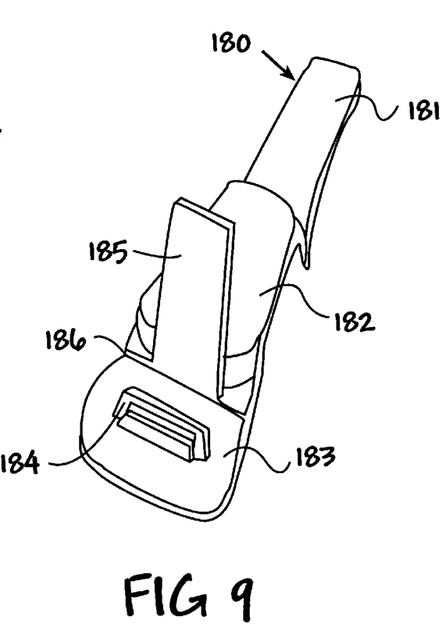
FIG. 9 is a perspective view of a support post according to the present invention.

FIG. 9 shows a support post 180 according to the present invention with a body 186, top portion 181, a mid portion 182 that projects up (as seen in FIG. 9) from the top portion 181 and a lower portion 183, and a hasp member 184 which projects through a corresponding slot of a shoe (not shown). A tongue 185 is hingedly connected to the body 186 and is sized and configured to project through the hasp member 184 to releasably hold the support post 180 to the shoe. As shown in FIG. 9 the support post 180 is resting on its side. When in place on a shoe, the support post 180 is upright, the tongue 185 is bent down; a portion of the tongue 185 is passed under and resides under the hasp member 184; and the hasp member 184 is projecting through the corresponding slot in a shoe.

Figure 13A:
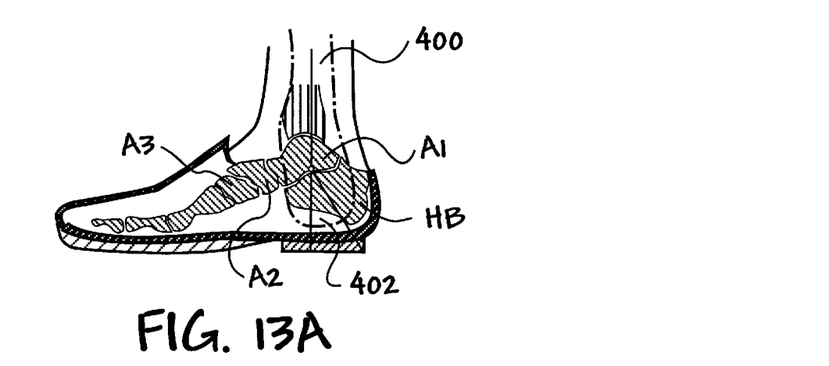
FIGS. 13A–D are side views in cross-section showing posts of supports according to the present invention.
Figure 13B:
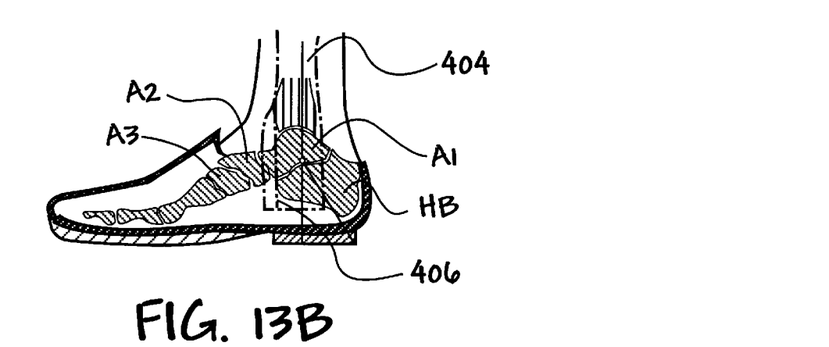
Figure 13C:
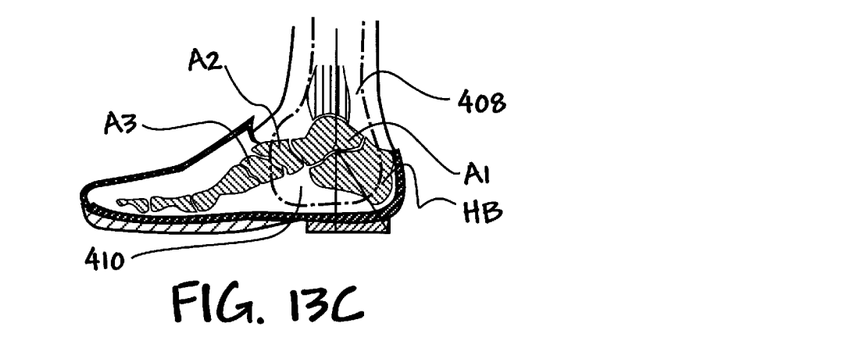
Figure 13D:
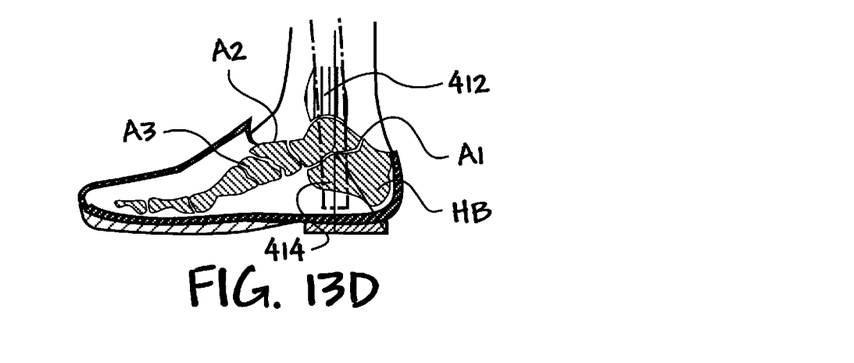

FIGS. 13A–13D illustrate support posts according to this invention with different width lower bases for use with feet in shoes, the feet having the bones as described below. For convenience the heel bone is designated as HB and other bones of the joint are designated as A1, A2 and A3 and these names are used in some of the claims that follow. FIG. 13A shows a post 400 with a lower portion 402 that extends from the heel bone to the bone A1 as viewed from the side. FIG. 13B shows a post 404 with a lower base 406 that extends from the heel bone to bone A2. FIG. 13C shows a post 408 with a lower base 410 that extends from the heel bone to the bone A3. FIG. 13D shows a post 412 that has a base 414 that extends from the heel bone to the bone A1.

Figure 14A:
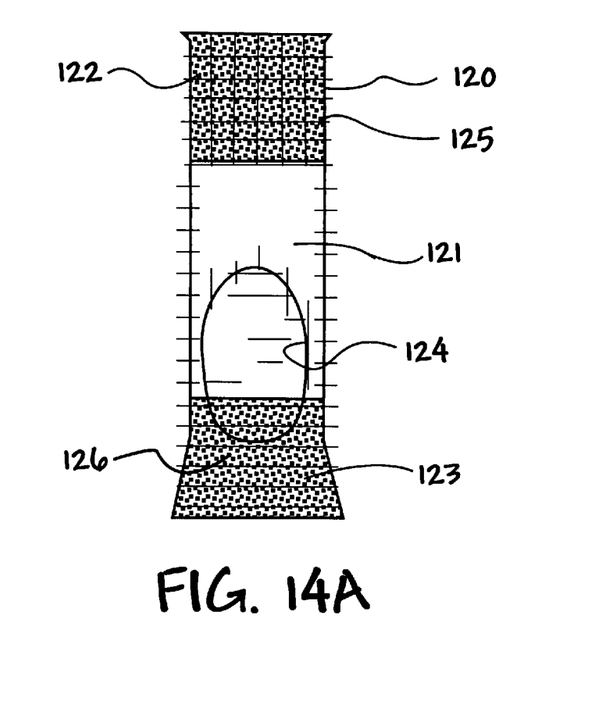
FIG. 14A is a front view of a support post according to the present invention.
Figure 14B:
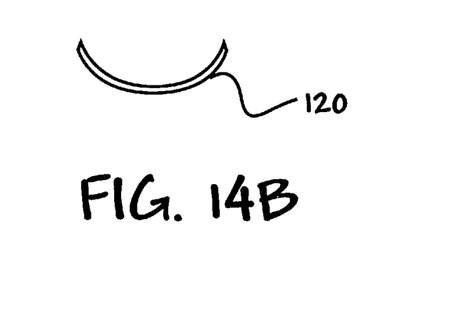
FIG. 14B is a top view of the support post of FIG. 14A.

FIG. 14A shows a support post 120 according to the present invention with a body 121, a top portion 122, a bottom portion 123, and a hole 124 through which part of a person's ankle bone may project. RCFM material 125 may be used on the top portion 122 and RCFM material 126 may be used on the bottom portion 123. Instead of a hole 124, a bubble or pushed-out portion of material may be used. Although, as shown in FIG. 14B, the support post 120 is slightly curved, it may be more curved or it may be flat.

Figure 15A:
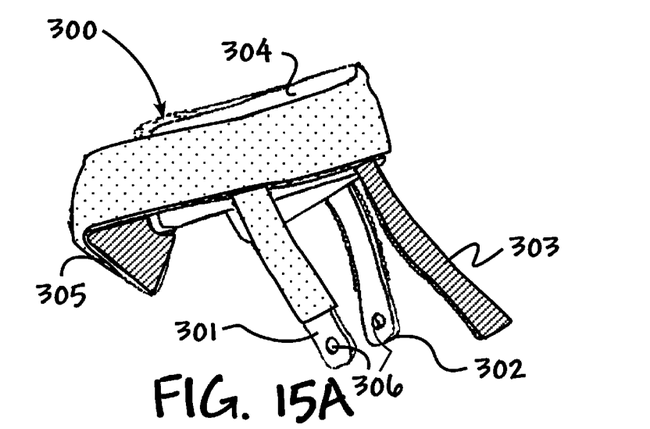
FIG. 15A is a perspective view of a device according to the present invention.
Figure 15B:
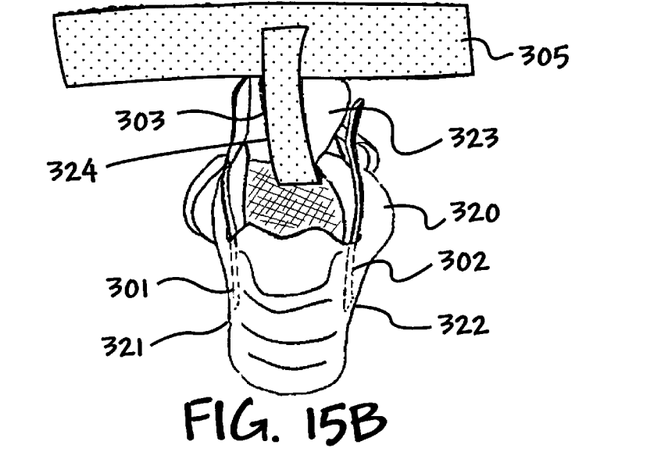
FIG. 15B is a rear view of the device of FIG. 15A with a shoe.
Figure 15C:
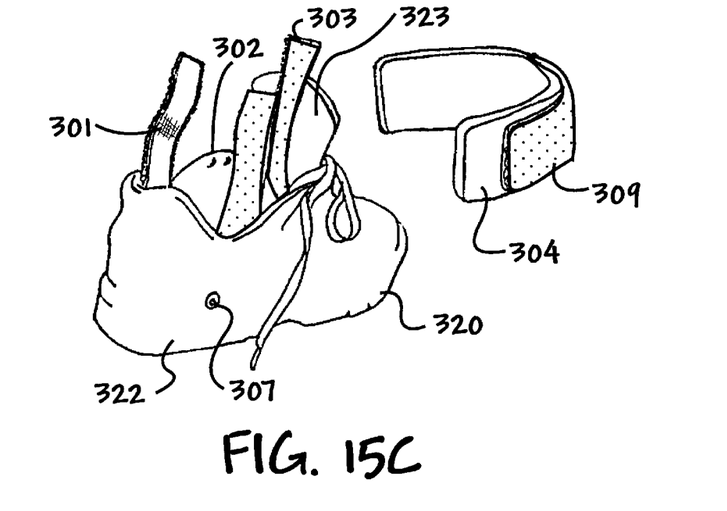
FIG. 15C is a side perspective view of the device and shoe of FIG. 15C.

FIGS. 15A–15C show a device 300 according to the present invention with two side posts 301, 302 and a front member 303. A cuff 304 encompasses a user's ankle (not shown) and a strap 305 holds upper portions of the side posts 301, 302 and of the front member 303. Holes 306 in the lower ends of the side posts 301, 302 receive fasteners (e.g. screws, bolts) not shown. The cuff 304 has a front portion 309 made of RCFM or VELCRO (TM) material.

The lower ends of the side posts 301, 302 may be slightly curved or rounded to facilitate movement with respect to an inner sole of a shoe.

A strap 305 is made of VELCRO (TM) material (understood herein to include any suitable releasable cooperating fastener material) on both sides and releasably attaches on one side to the front portion 309 of the cuff 304. The top side of the front member 303 has corresponding material as do the outer portions of the tops of the side posts 301, 302. Thus the strap 305 releasably holds the tops of the posts 301, 302 and of the front member 303. The portion 309 may be glued and/or sewn onto the cuff 304.

In one particular embodiment the cuff 304 is about ½ to ¾ inches thick and is made of open or closed cell foam, e.g. as commercially available from AASP Co., Houston, Tex.

FIG. 15C shows fasteners 307 securing the side posts 301, 302 to sides 321, 322 of a shoe 320. The front member 305 has suitable VELCRO (TM) material 324 on its top side so that it releasably holds to the lower inner surface of a tongue 323 of the shoe 320. This surface is made of fabric that releasably mates with the material 324.

Figures 15D, 15E, 15F, 15G:
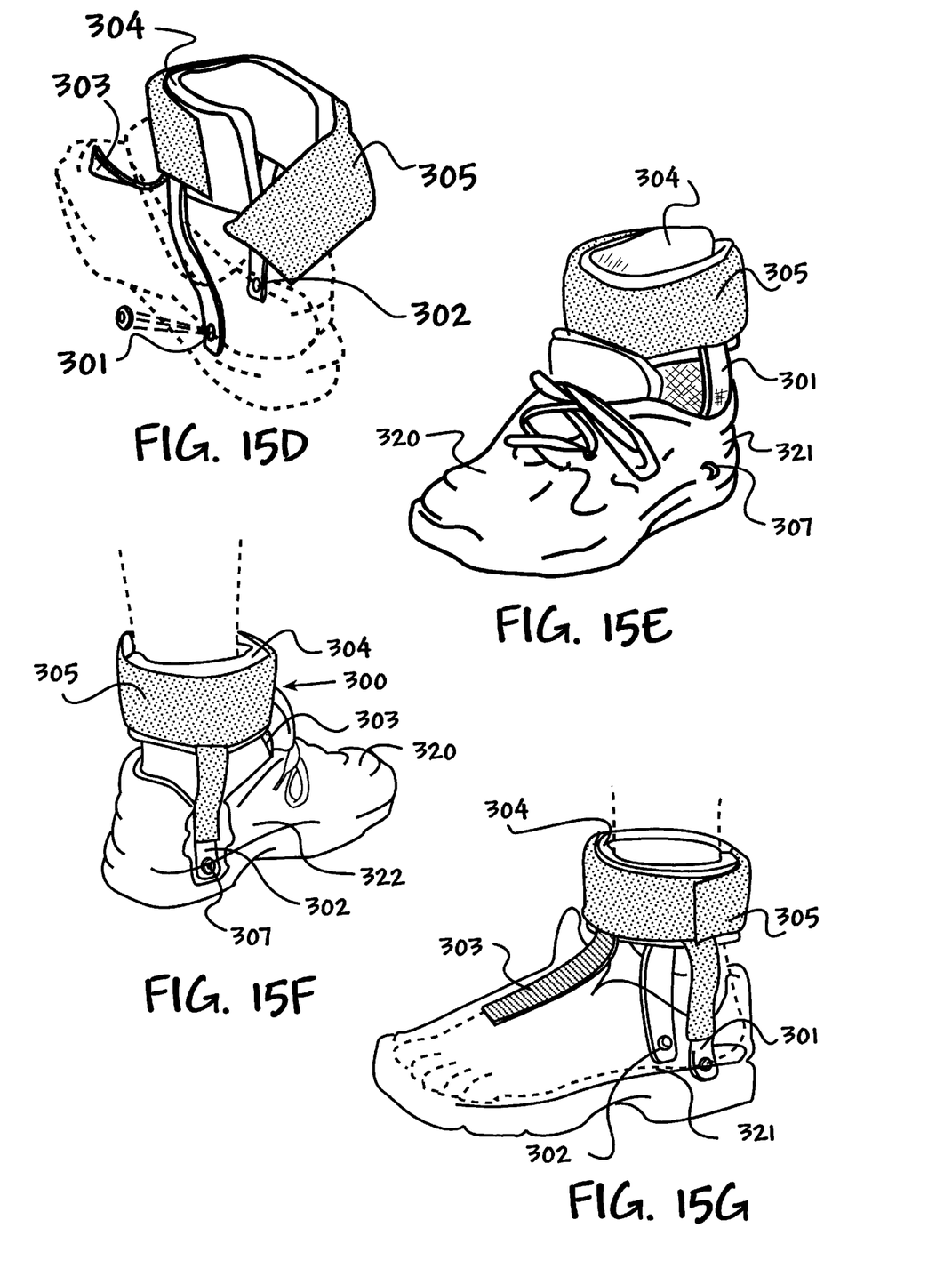
FIG. 15D–15F are side perspective views of the device and shoe of FIG. 15A.
FIG. 15G is a side view of the device of FIG. 15A with a shoe.

FIG. 15D shows that the strap 305 may be of such a length that it is easily adjusted around a person's ankle for a snug yet comfortable fit.

FIGS. 15F and 15G show the device 300 with the cuff 304 around a user's ankle.

Figure 16A:
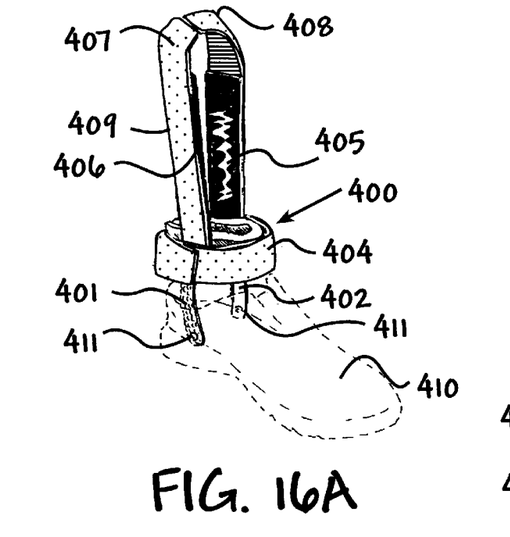
FIG. 16A is a side perspective view of a foot support device according to the present invention.

FIG. 16A shows a system 400 according to the present invention with side posts 401, 402 (like the posts 301, 302 of the system 300) movably connected to a shoe 410 with connectors 411, cuff 404 (like the cuff 304 of system 300). Bars 405, 406 have VELCRO (TM) material 409 thereon with portions 407, 408 thereabove. Optionally the bars 405, 406 are secured with fasteners 407 to the cuff 404. Optionally a front member, not shown, like the front member 303, system 300) may be used. Optionally one or both bars may be deleted and VELCRO (TM) material alone used; and/or the bars which are rigid may be replaced with flexible foam material. Alternatively only one bar and/or only one piece of VELCRO (TM) material may be used.

Figure 16B:
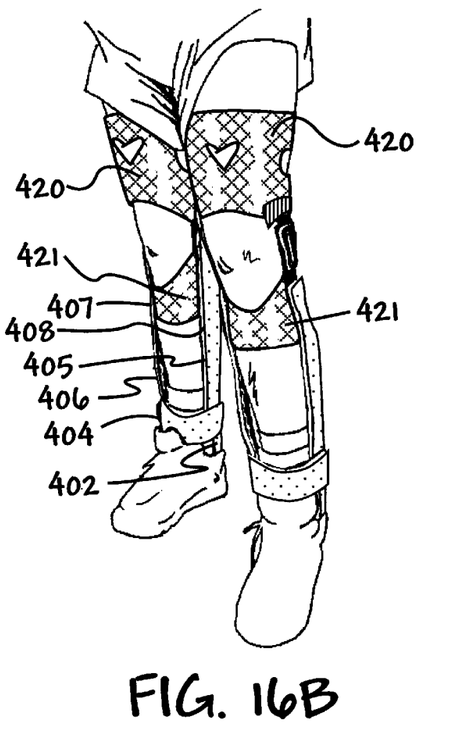
FIG. 16B is a front perspective view of a foot support/knee brace device according to the present invention.
Figure 16C:
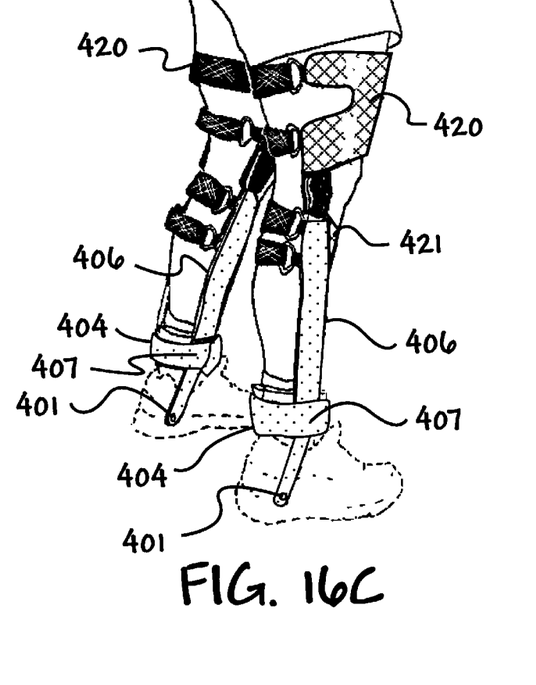
FIG. 16C is a rear perspective view of a foot support/knee brace device according to FIG. 16B.

As shown in FIGS. 16B and 16C, a system according to the present invention may include a system 400 with its upper Velcro™ portions 407, 408 releasably connected to corresponding material 421 of typical known knee braces 420. This interconnection helps to maintain the knee braces in a desired position and relationship to a wearer's knee without unwanted slippage down a wearer's leg.

Photographs 17A–17D show the device 300 with shoes S according to the present invention.

Figure 17A:
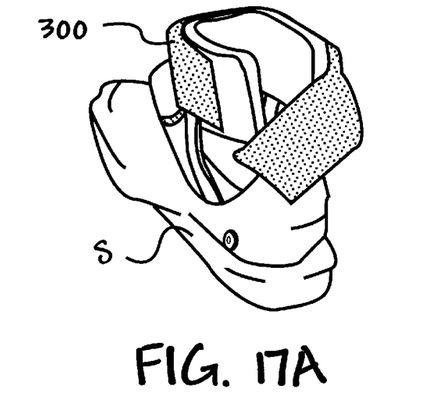
Figure 17B:
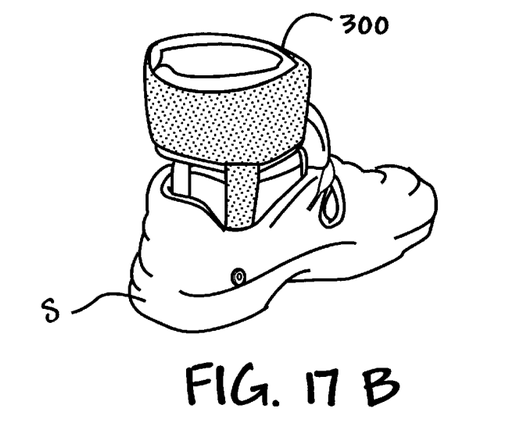
Figure 17C:
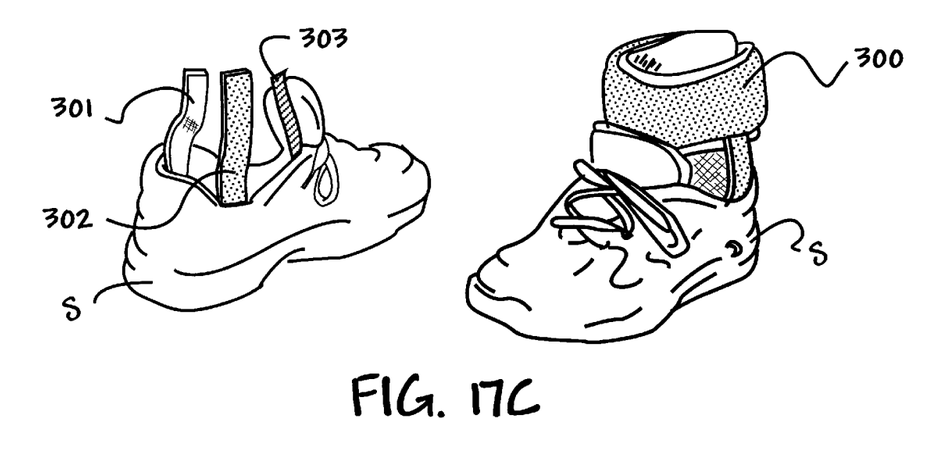
Figure 17D:
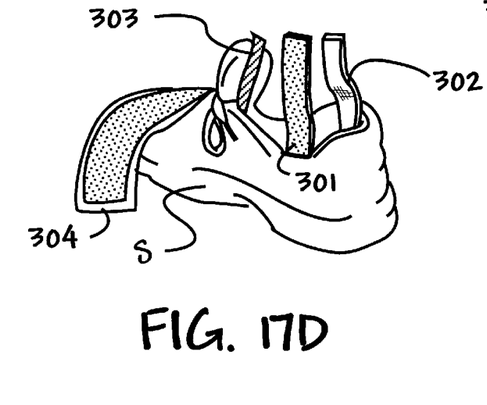
Figure 17E:
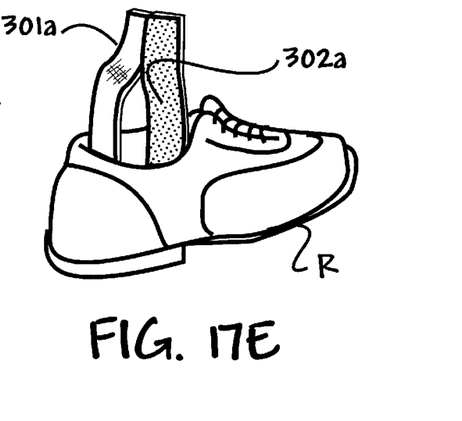
Figure 17F:
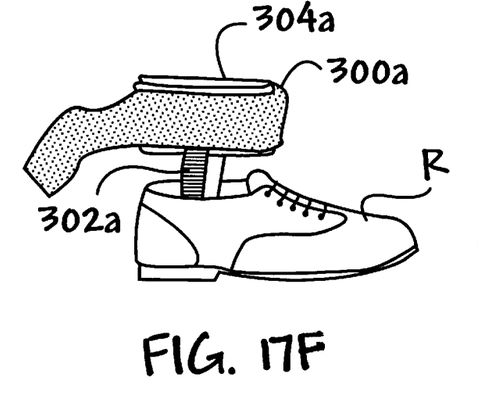
Figure 17G:
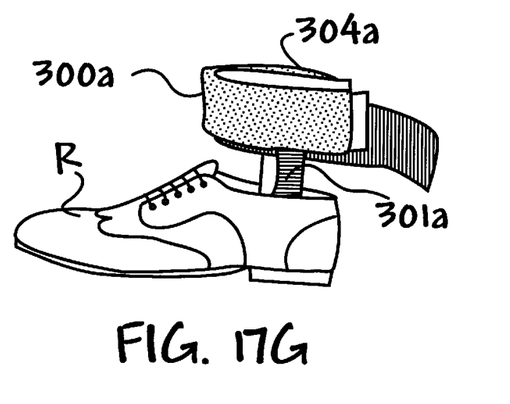

Photographs 17E–17G show a device 300a with posts 301a and 302a and a cuff 304a (like the device 300) with another style shoe R.

Figure 17H:
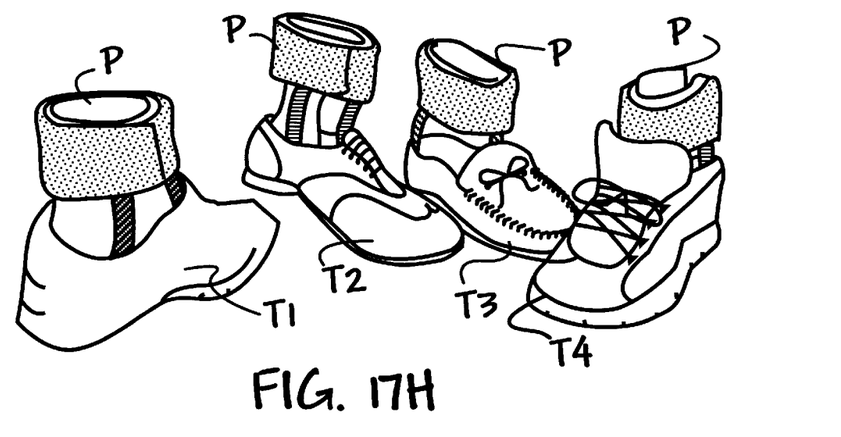

Photograph 17H show various shoe designs T1, T2, T3, T4 with devices P according to the present invention.

Figure 18A:
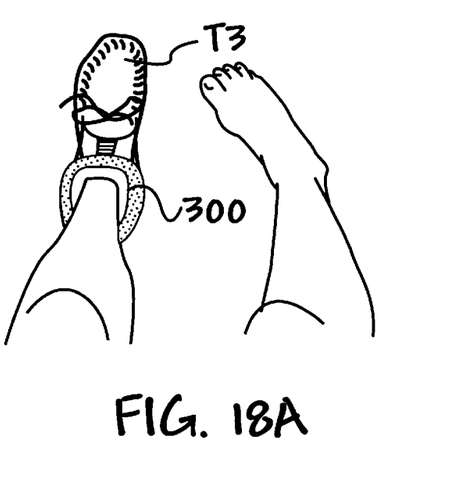

Photograph 18A shows a shoe design T3 and device 300 (like the devices 300, 300a) according to the present invention on the foot of a person afflicted with drop foot.

Figure 18B:
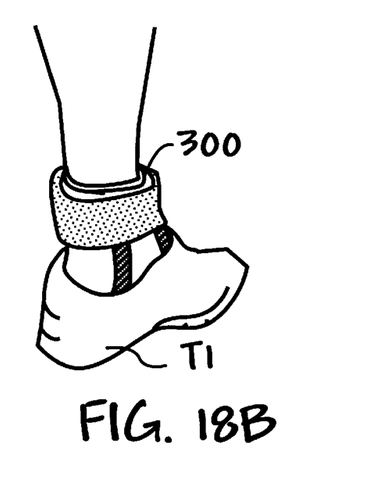

Photograph 18B shows the device 300 with a shoe T1 on a user of the device.

The present invention therefore, provides in certain embodiments, a foot support device for use with a shoe, the foot support device having two spaced-apart side posts, each having a bottom end connectible to a side of the shoe and a top end, a front member having a top end and a bottom end connectible to a top part of the shoe and spaced-apart from each of the side posts, and a cuff for emplacement about a leg of a wearer, the cuff connected permanently or releasably to the top ends of the two side posts and to the top of the front member; such a foot support device wherein the cuff is made of foam material; such a foot support device with a strap for wrapping around the cuff to secure the cuff around a wearer's leg; such a foot support device with an amount of releasably cooperating fastener material on an outer surface of the cuff, and a corresponding amount of releasably cooperating fastener material on an inner surface of the strap for facilitating securement of the strap around the cuff; such a foot support device with an amount of releasably cooperating fastener material on an outer surface of the strap for releasable securement thereto of at least part of the amount of releasably cooperating fastener material on the inner surface of the strap; such a foot support device wherein each side post has a curved portion for accommodating part of an ankle of a wearer of the foot support device; such a foot support device wherein the front member is flexible; and/or such a foot support device wherein the front member has an amount of releasably cooperating fastener material thereon suitable for releasable fastening to the top part of the shoe, the shoe with corresponding releasably cooperating fastener material thereon or the shoe made with material on a top portion thereof that releasably cooperates with the material on the front member. In other aspects any such foot support device is used in anew combination with a knee brace releasably securable about a knee of a person wearing a shoe to which is connected the foot support device, the foot support device having at least one connecting member for releasable interconnection to and between the brace and the foot support device; and such a combination wherein the at least one connecting member is two spaced-apart connecting members, one on each side of the shoe.

The present invention, therefore, provides, in certain embodiments, a method for supporting a foot on a leg of a person, the method including emplacing the foot in a shoe, the shoe having connected thereto any foot support device disclosed herein, including but not limited to such a device with two spaced-apart side posts, each having a bottom end connected to a side of the shoe and a top end, a front member having a top end and a bottom end connected to a top part of the shoe and spaced-apart from each of the side posts, and a cuff emplacable about a leg of the person, the cuff connected to the top ends of the two side posts and to the top of the front member, and securing the cuff around a part of the leg of the person; and such a method wherein the foot support device includes a knee brace releasably securable about a knee of the person wearing the shoe to which is connected the foot support device, the foot support device having at least one connecting member for interconnecting to and between the brace and the foot support device, the method including securing the knee brace about the person's knee, and interconnecting the knee brace and the foot support device with the at least one connecting member.

In conclusion, therefore, it is seen that the present invention and the embodiments disclosed herein and those covered by the appended claims are well adapted to carry out the objectives and obtain the ends set forth. Certain changes can be made in the subject matter without departing from the spirit and the scope of this invention. It is realized that changes are possible within the scope of this invention and it is further intended that each element or step recited in any of the following claims is to be understood as referring to all equivalent elements or steps. The following claims are intended to cover the invention as broadly as legally possible in whatever form it may be utilized. The invention claimed herein is new and novel in accordance with 35 U.S.C. § 102 and satisfies the conditions for patentability in § 102. The invention claimed herein is not obvious in accordance with 35 U.S.C. § 103 and satisfies the conditions for patentability in § 103. This specification and the claims that follow are in accordance with all of the requirements of 35 U.S.C. § 112.

What is claimed is:

1. A method for supporting a foot on a leg of a person, the method comprising emplacing the foot in a shoe, the shoe having connected thereto a foot support device comprising two spaced-apart side posts, each having a bottom end connected to a side of the shoe and a top end, a front member having a top end and a bottom end releasably connected to a top part of the shoe and spaced-apart from each of the side posts, and a cuff releasably emplaced about a leg of the person, the cuff releasably connected to the top ends of the two side posts and to the top of the front member, securing the cuff around a part of the leg of the person, wherein the foot support device further comprises a knee brace releasably securable about a knee of the person wearing the shoe to which is connected the foot support device, the foot support device having at least one connecting member for releasably interconnected to and between the brace and the foot support device, the method further comprising securing the knee brace about the person's knee, and releasably interconnecting the knee brace and the foot support device with the at least one connecting member.

2. The method of claim 1 wherein the cuff is made of foam material.

3. The method of claim 1 wherein the foot support device has a strap secured to the cuff and sized and configured to wrap around the person's leg, the method further comprising using the strap to facilitate securement of the cuff around the person's leg.

4. The method of claim 3 wherein there is an amount of releasably cooperating fastener material on an outer surface of the cuff, and a corresponding amount of releasably cooperating fastener material on an inner surface of the strap for facilitating securement of the strap around the cuff.

5. The method of claim 4 wherein there is an amount of releasably cooperating fastener material on an outer surface of the strap for releasable securement thereto of at least part of the amount of releasably cooperating fastener material on the inner surface of the strap.

6. The method of claim 1 wherein each side post has a curved portion for accommodating part of an ankle of the person wearing the foot support device, the method further comprising accommodating part of the person's ankle with each side post's curved portion.

7. The method of claim 1 wherein the front member is flexible.

8. The method of claim 7 wherein the front member has an amount of releasably cooperating fastener material thereon suitable for releasable fastening to the top part of the shoe, and the method further comprising releasably fastening the amount of releasably cooperating fastener material on the front member to the top part of the shoe.

9. The method of claim 1 wherein the at least one connecting member is two spaced-apart connecting members, one on each side of the shoe.

* * * * *